United States Patent
Muraoka et al.

(10) Patent No.: US 7,329,665 B2
(45) Date of Patent: Feb. 12, 2008

(54) QUINAZOLINONE DERIVATIVE

(75) Inventors: Masami Muraoka, Suita (JP); Kazuki Matsui, Sanda (JP); Takaaki Yamamoto, Kobe (JP); Koji Morishita, Nishinomiya (JP); Masatoshi Yuri, Ushiku (JP); Seiji Katayama, Toyonaka (JP); Naohito Ohashi, Takatsuki (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 537 days.

(21) Appl. No.: 10/485,865

(22) PCT Filed: Aug. 2, 2002

(86) PCT No.: PCT/JP02/07930

§ 371 (c)(1),
(2), (4) Date: Sep. 27, 2004

(87) PCT Pub. No.: WO03/016299

PCT Pub. Date: Feb. 27, 2003

(65) Prior Publication Data

US 2005/0032819 A1    Feb. 10, 2005

(30) Foreign Application Priority Data

Aug. 9, 2001  (JP) .............................. 2001-241955

(51) Int. Cl.
*A61K 31/517* (2006.01)
*C07D 401/04* (2006.01)
*C07D 239/82* (2006.01)
*C07D 239/80* (2006.01)

(52) U.S. Cl. .................. 514/266.22; 544/284; 544/286

(58) Field of Classification Search .......... 514/266.22; 544/284, 286
See application file for complete search history.

(56) References Cited

U.S. PATENT DOCUMENTS 5,556,860 A * 9/1996 Muraoka et al. .......... 514/258.1
6,645,971 B1 * 11/2003 Muraoka et al. ....... 514/266.22

FOREIGN PATENT DOCUMENTS

| EP | 0 626 373 A1 | 11/1994 |
| EP | 1 122 253 A1 | 8/2001 |
| WO | 00/23436 A1 | 4/2000 |

OTHER PUBLICATIONS

International Search Report dated Oct. 2, 2002.

* cited by examiner

*Primary Examiner*—James O. Wilson
*Assistant Examiner*—Tamthom N Truong
(74) *Attorney, Agent, or Firm*—Sughrue Mion, Pllc.

(57) ABSTRACT

An optically active form of the quinazolinone derivatives represented by the general formula (1):

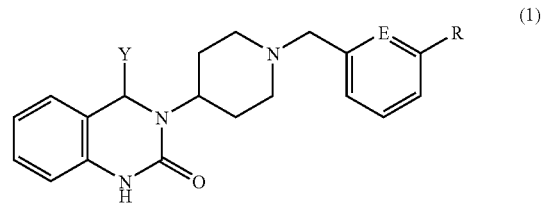

[wherein Y represents a phenyl group or C2-C7 alkyl group; E represents —CH= or nitrogen atom; and R represents a C1-C4 alkyl group and so on], or pharmaceutically acceptable salts thereof, has a selective antagonism for the M3 muscarinic receptor and depressant action on the frequency of rhythmic bladder contractions, and it is useful for the treatment of pollakiuria and urinary incontinence.

12 Claims, No Drawings

QUINAZOLINONE DERIVATIVE

TECHNICAL FIELD

The present invention relates to optically active 3,4,-dihydro-2(1H)-quinazolinone derivatives, production method thereof, medicaments containing them and their use for medicaments, especially, remedy for pollakiuria and urinary incontinence.

BACKGROUND ART

Oxybutinin is used as a medicament having an antagonistic action on muscarinic receptors for the treatment of pollakiuria and urinary incontinence, while the medicament is known to be inevitably associated with side effects due to its antagonistic action on muscarinic receptors.

There are at least three known subtypes of muscarinic receptors which are the sites of action of anticholinergic drugs, and it has been shown that the M1 receptor is mainly localized in the brain, the M2 receptor in the heart, and the M3 receptor in smooth muscle and the glandular tissue, respectively. Accordingly, when a compound having an antagonistic action on muscarinic receptors is used as a remedy for the treatment of pollakiuria and urinary incontinence, it is considered preferable that the selectivity for the M3 receptor is higher than that for the M1 and M2 receptors, and compounds with a variety of chemical structures, that is selective for the M3 receptor, have been reported.

However, dry mouth and mydriasis which are generally-known side effects of anticholinergic drugs result from the antagonistic action on the M3-receptor, and thus it is difficult to eliminate these side effects merely by enhancing the selectivity for the M3 receptor. On the other hand, research and development of non-cholinergic remedies for the treatment of pollakiuria and urinary incontinence, such as α-receptor regulator, potassium channel opener and central muscular relaxtation action, are proceeding, but no medicament having a satisfactory effect has been obtained.

Accordingly, it is desired to obtain a compound that has another useful action for the treatment of pollakiuria and urinary incontinence in addition to the antagonistic action on the muscarinic receptor as the compound which can be widely used for the treatment of pollakiuria and urinary incontinence and which can reduce the side effects of anticholinergic medicaments, due to having a plurality of actions.

On the other hand, quinazolinone derivatives have been reported as the compound having a selective antagonism for the M3 muscarinic receptor in WO 00/23436.

DISCLOSURE OF INVENTION

An object of the present invention is to provide a compound having another useful action for the treatment of pollakiuria and urinary incontinence in addition to the selective antagonism for the M3 muscarinic receptor as the compound which can be widely used for the treatment of pollakiuria and urinary incontinence and which may reduce the side effects of anticholinergic medicaments.

The present inventors have made an earnest study to solve the above problem and have now found that an optically active form of the quinazolinone derivatives represented by the following general formula (1) or pharmaceutically acceptable salts thereof (hereinafter abbreviated as the compounds of the present invention as appropriate) not only has the selective antagonism for the M3 muscarinic receptor but also newly has a depressant action on the frequency of rhythmic bladder contractions, completing the present invention.

Furthermore, the compounds of the present invention have been found to have a depressant action on afferent nerve activation. This action is considered to be useful for the treatment of pollakiuria and urinary incontinence.

The present invention relates to the followings:

[1] An optically active form of the quinazolinone derivatives represented by the general formula (1):

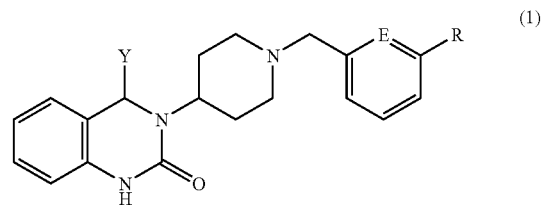

[wherein Y represents a phenyl group or C2-C7 alkyl group; E represents a group of the formula —CH= or nitrogen atom; and R represents a fluorine atom, C1-C4 alkyl group, C1-C4 alkoxy group, trifluoromethoxy group or 2,2,2-trifluoroethoxy group], or pharmaceutically acceptable salt thereof.

[2] The optically active form of the quinazolinone derivatives described in [1], which is (+) form, or pharmaceutically acceptable salt thereof.

[3] The optically active form of the quinazolinone derivatives described in [1] or [2], wherein Y is a phenyl group and E is a group of the formula —CH=, or pharmaceutically acceptable salt thereof.

[4] The optically active form of the quinazolinone derivatives described in [1] or [2], wherein Y is a C2-C7 alkyl group and E is a nitrogen atom, or pharmaceutically acceptable salt thereof.

[5] The optically active form of the quinazolinone derivatives described in any of [1] to [4], wherein Y is a C3-C7 alkyl group, or pharmaceutically acceptable salt thereof.

[6] (+)-3-{1-[3-(2,2,2-trifluoroethoxy)benzyl]piperidin-4-yl}-4-phenyl-3, 4-dihydro-2(1H)-quinazolinone or pharmaceutically acceptable salt thereof.

[7] (+)-3-[1-(3-trifluoromethoxybenzyl)piperidin-4-yl]-4-phenyl-3,4-dihydro-2(1H)-quinazolinone or pharmaceutically acceptable salt thereof.

[8] (+)-4-isopropyl-3-{1-[(6-methyl-2-pyridinyl)methyl]piperidin-4-yl}-3, 4-dihydro-2(1H)-quinazolinone or pharmaceutically acceptable salt thereof.

[9] (+)-3-[1-(3-trifluoromethoxybenzyl)piperidin-4-yl]-4-phenyl-3,4-dihydro-2(1H)-quinazolinone fumarate.

[10] A medicament comprising the compound described in any of [1] to [9] or pharmaceutically acceptable salt thereof.

[11] A remedy for treating pollakiuria or urinary incontinence comprising the compound described in any of [1] to [9] or pharmaceutically acceptable salt thereof as an active ingredient.

Various groups concerning the present invention are explained in detail below.

The C2-C7 alkyl group can be straight chain or branched and typical examples include ethyl, propyl, isopropyl, butyl, isobutyl, pentyl, hexyl and 4-heptyl.

The C1-C4 alkyl group and the alkyl part in the C1-C4 alkoxy group can be straight chain or branched and typical examples include methyl, ethyl, propyl, butyl and isopropyl.

The compounds of the present invention include adducts with solvent, for example, hydrate and alcohol adducts (e.g. ethanolate).

The quinazolinone derivatives or pharmaceutically acceptable salts thereof of the present invention can be produced by the methods below.

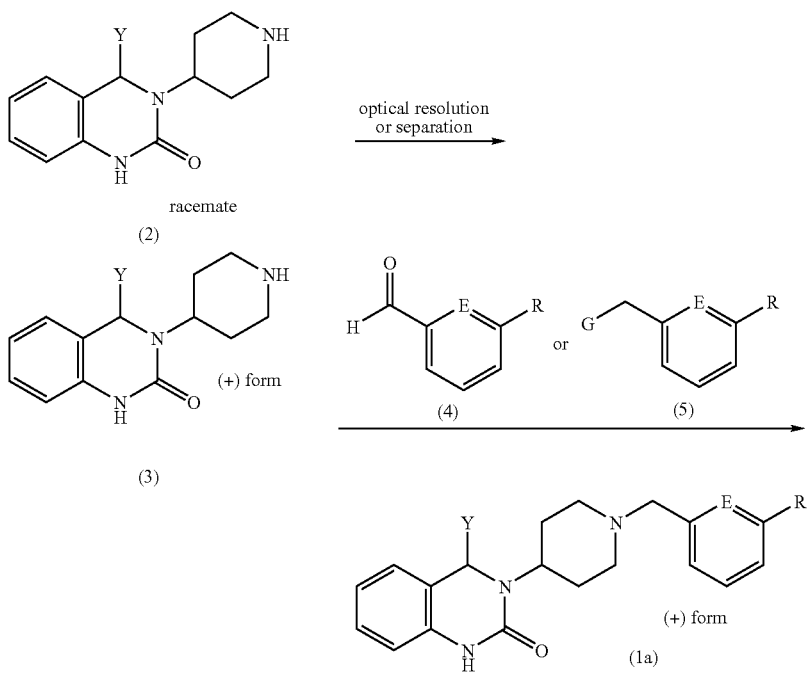

[wherein Y, E and R have the same meanings above and G represents a leaving group]

The optically active form (3) can be isolated from the racemic compound given by the general formula (2) by optical resolution or separation with high pressure liquid chromatography having a column for separating optical isomers. The optical resolution can be carried out by conventional method using an optically active acid as an optical resolving reagent and sometimes by preferential crystallization. In case that Y is a phenyl group, preferable optical resolving reagent for (+) form is N-benzoyl-D-phenylalanine.

Then, the optically active compound (1a) can be obtained by making the compound (3) react with the aldehyde derivative (4) or the compound (5) according to known methods. The reaction with the aldehyde derivative (4) is a reductive alkylation and can be carried out by treating the compound (3) and 1 to 5 equivalents of the aldehyde derivative (4) with 1 to 5 equivalents of a reducing agent at 0-50° C. in a solvent. It is preferably carried out by using sodium borohydride (NaBH₄), sodium cyanoborohydride (NaBH₃CN) or sodium triacetoxyborohydride (NaB(OCOCH₃)₃H) as a reducing agent. Any solvent that does not interfere the reaction can be used and the reaction is preferably carried out by using alcohol solvents such as methanol and ethanol, or halogenated solvents such as dichloromethane and 1,2-dichloroethane.

The alkylation reaction can be carried out by making the compound (3) react with the alkylation agent given by the general formula (5) in a solvent. The reaction is usually carried out in a solvent at 0-100° C., preferably at room temperature to 70° C., in the presence of a base if necessary. Examples of the solvent include ether solvents such as tetrahydrofuran and dioxane; aromatic hydrocarbon solvents such as benzene and toluene; ketone solvents such as acetone and 2-butanone; and dimethylformamide. Examples of the base include sodium hydride, potassium carbonate, sodium carbonate and triethylamine. When potassium carbonate or sodium carbonate is used, an addition of sodium iodide or potassium iodide may increase yield. Examples of the leaving group given by G include halogen atoms such as chlorine, bromine and iodine; aromatic sulfonyloxy group such as benzenesulfonyloxy group and p-toluenesulfonyloxy group; and methanesulfonyloxy group.

Further, the optically active compound (1a) can also be produced by the method below.

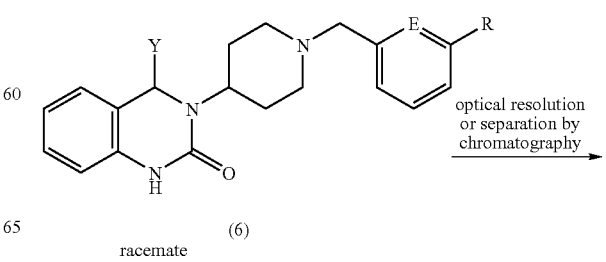

-continued

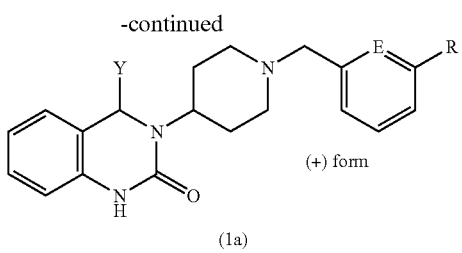

(1a) (+) form

[wherein Y, E and R have the same meanings above]

The racemate (6) can be produced from the racemate (2) by the same conversion as one from the compound (3) to the compound (1a) and then the optically active compound (1a) can be isolated from the racemate (6) by an optical resolution or separation by high pressure liquid chromatography with a column for separating optical isomers. The optical resolution can be carried out by a conventional method using an optically active acid as an optical resolving reagent and may be carried out by preferential crystallization.

In the present invention, pharmaceutically acceptable salts are, for example, salts with inorganic acids or organic acids. Examples of the inorganic acid include hydrochloric acid, hydrobromic acid, nitric acid, sulfuric acid and phosphoric acid; and examples of the organic acid include formic acid, acetic acid, propionic acid, lactic acid, tartaric acid, oxalic acid, fumaric acid, maleic acid, citric acid, malonic acid, methanesulfonic acid and benzenesulfonic acid. These salts are prepared by conventional methods, for example, by mixing with the above-mentioned acid in a solvent (e.g. water, methanol, ethanol, acetone).

The racemic compounds (1) and (2) are prepared according to the methods described in JP 7-215943A, and the compound (2) is also prepared by the following method.

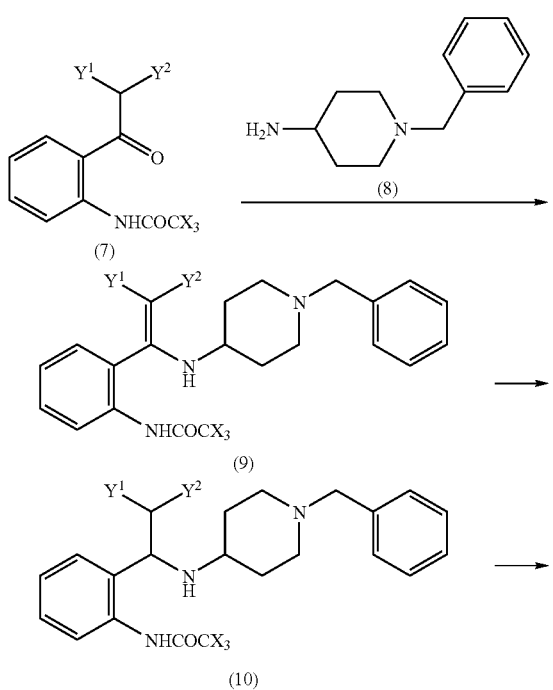

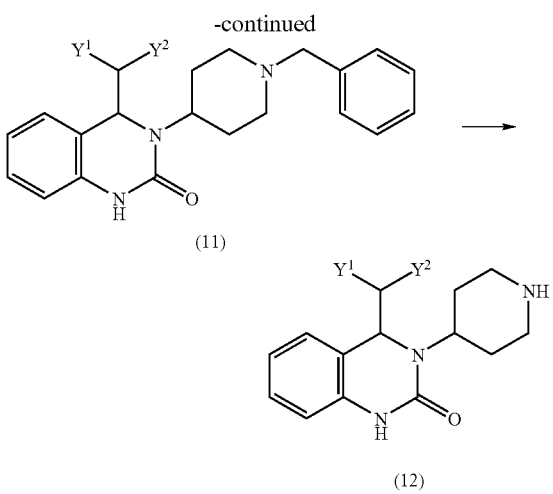

[wherein $Y^1$ and $Y^2$ independently represent a methyl, ethyl, propyl or isopropyl group, and X represents a chlorine atom or bromine atom]

The compound (9) is obtained by condensing the ketone derivative given by the formula (7) with the amine derivative (8) in the presence of titanium tetrachloride. In the reaction, 1 to 3 equivalents of the amine derivative (8) and 1 to 2 equivalents of the titanium tetrachloride, and if necessary 1 to 5 equivalents of a base such as triethylamine, are used based on 1 mol of the ketone compound given by the general formula (7), and the mixture is stirred at 0° C. to room temperature. Preferable solvents are ethers such as tetrahydrofuran. Then, the obtained compound (9) was reduced to give the compound (10). By using sodium borohydride ($NaBH_4$), sodium cyanoborohydride ($NaBH_3CN$) or sodium triacetoxyborohydride ($NaB(OCOCH_3)_3H$) as a reducing agent, the reduction is well carried out. Any solvent that does not interfere the reaction can be used and the reaction is preferably carried out by using alcohol solvents such as methanol and ethanol, halogenated solvents such as dichloromethane and 1,2-dichloroethane or ether solvents such as tetrahydrofuran. The compound (11) can be produced by heating the compound (10) in the presence of potassium carbonate or sodium carbonate at 50 to 100° C. usually in a solvent. The conversion from the compound (11) to the compound (12) can be carried out according to the description of JP 7-215943A.

When the compounds of the present invention are used as a medicament, these may be administered orally or parenterally. That is, these may be orally administered in dosage forms that are conventionally used, such as powders, granules, tablets, capsules, syrups and suspensions, or a preparation of their solution, emulsion or suspension may be parenterally administered in injection forms. Rectal administration may also be done in a suppository form. The above dosage forms suitable for administration may be prepared by formulating the compounds of the present invention with, for example, acceptable conventional carriers, excipients, binders, stabilizers and diluents. When the compounds are used in an injection form, for example, acceptable buffers, solubilizing agents and isotonizing agents may also be added. The dose level and frequency may be varied depending upon, for example, the disease to be treated, the symptom, the age, the body weight and the dosage form, and may be from 0.1 to 2000 mg per day as the total daily dose for an adult, preferably from 1 to 200 mg, once or several times a day (e.g. 2 to 4 times a day).

EXAMPLES

Hereinafter, the present invention is explained by reference examples, examples and test example in more detail; however the present invention does not restricted by them.

Example 1

Production of (+)-3-{1-[3-(trifluoromethoxy)benzyl]piperidin-4-yl}-4-phenyl-3,4-dihydro-2(1H)-quinazolinone a) Production of (+)-3-(piperidin-4-yl)-4-phenyl-3,4-dihydro-2(1H)-quinazolinone In 600 ml of 2-propanol, 10.0 g (32.5 mmol) of racemic 3-(piperidin-4-yl)-4-phenyl-3,4-dihydro-2(1H)-quinazolinone were dissolved under heating. At about 60° C., 8.76 g (32.5 mmol) of N-benzoyl-D-phenylalanine were added thereto and refluxed under heating. After allowing to stand to cool, the precipitated crystals were filtered to give 11.9 g of N-benzoyl-D-phenylalanine salt of 3-(piperidin-4-yl)-4-phenyl-3,4-dihydro-2(1H)-quinazolinone.

The obtained salt was recrystallized from a mixed solvent of 120 ml of methanol and 1150 ml of 2-propanol to give 9.7 g of the recovered salt, which was followed by further recrystallization from 100 ml of methanol and 900 ml of 2-propanol to give 7.88 g of the salt.

The salt obtained above was separated between 120 ml of chloroform and 120 ml of 0.5N—NaOH aqueous solution, and the chloroform layer was washed with 0.5N—NaOH aqueous solution, dried over anhydrous sodium sulfate and then concentrated under reduced pressure. The concentrated residue was subjected to recrystallization from 320 ml of acetonitrile to give 3.3 g of the above-titled compound.

$[\alpha]_D^{25}$+250.2° (c=1, methanol)

b) Production of (+)-3-[1-(3-trifluoromethoxybenzyl)piperidin-4-yl]-4-phenyl-3,4-dihydro-2(1H)-quinazolinone Into a solution of 36.0 g (117 mmol) of (+)-3-(piperidin-4-yl)-4-phenyl-3,4-dihydro-2(1H)-quinazolinone and 24.5 g (190 mmol) of 3-trifluoromethoxybenzaldehyde in 500 ml of dichloromethane, 54.6 g (129 mmol) of sodium triacetoxyborohydride were added at room temperature and stirred for 16 hours. Five hundred milliliters (500 ml) of water, 100 ml of conc. aqueous ammonia and 500 ml of chloroform were added thereto, and stirred. The separated oil layer was washed with saturated brine, dried over anhydrous sodium sulfate and concentrated under reduced pressure. The concentrated residue was purified by silica gel chromatography (hexane/ethyl acetate 5/1) to give 51.7 g (114 mmol) of the above-titled compound.

Into a solution of 4.00 g of the above-titled compound in 47 ml of 2-propanol, 1.44 g of fumaric acid were added and heated under stirring. After confirming that the crystals were dissolved, 47 ml of heptane were added thereto and cooled. The precipitated crystals were filtered to give 4.73 g of a 2:3 salt of the above-titled compound and fumaric acid.

mp: 196-197° C. $[\alpha]_D^{25}$+126.4° (c=1, methanol) Elemental analysis: Calculated values C, 60.45; H, 4.92; F, 8.69; N, 6.41. Experimental values C, 60.37; H, 5.08; F, 8.63; N, 6.40 for $C_{66}H_{64}F_6N_6O_{16}$.

After 0.38 ml of 1N hydrochloric acid/ether solution was added into an isopropanol solution containing 150 mg of the above-titled compound and stirred, the mixture was concentrated under reduced pressure. Isopropyl ether was added to the concentrated residue and stirred. The precipitated crystals were filtered to give 130 mg of the above-titled compound hydrochloride.

mp: 195-198° C.

By the similar procedures to Example 1b), the compounds below were produced from (+)-3-(piperidin-4-yl)-4-phenyl-3,4-dihydro-2(1H)-quinazolinone.

Example 2-1

Optically Active Form of 3-[1-(3-propylphenylmethyl)piperidin-4-yl]-4-phenyl-3,4-dihydro-2(1H)-quinazolinone $^1$H-NMR δ (CDCl$_3$): 0.92 (3H, t, J=7.3 Hz), 2.55 (2H, t, J=7.7 Hz), 3.44 (2H, s), 4.38-4.45 (1H, m), 5.57 (1H, s), 6.75 (1H, d, J=7.7 Hz), 7.38-7.41 (2H, m), 8.39 (1H, brs)

Example 2-2

Optically Active Form of 3-[1-(3-propoxyphenylmethyl)piperidin-4-yl]-4-phenyl-3,4-dihydro-2(1H)-quinazolinone $^1$H-NMR δ (CDCl$_3$): 1.03 (3H, t, J=7.4 Hz), 3.43 (2H, s), 5.56 (1H, s), 6.75-6.94 (5H, m), 7.07-7.28 (6H, m), 8.45 (1H, s)

Example 2-3

Optically Active Form of 3-[1-(3-isopropoxyphenylmethyl)piperidin-4-yl]-4-phenyl-3,4-dihydro-2(1H)-quinazolinone $^1$H-NMR δ (CDCl$_3$): 1.32 (6h, dd, J=6.0 Hz, 2.1 Hz), 3.42 (2H, s), 5.56 (1H, s), 6.75-6.90 (5H, m), 8.57 (1H, s)

Example 2-4

Optically Active Form of 3-{1-[3-(2,2,2-trifluoroethoxy)phenylmethyl]piperidin-4-yl}-4-phenyl-3,4-dihydro-2(1H)-quinazolinone $^1$H-NMR δ (CDCl$_3$): 3.43 (2H, s), 4.31 (2H, q, J=8.2 Hz), 5.57 (1H, s), 6.78-6.96 (5H, m), 8.89 (1H, s)

Example 3

Production of (+)-4-isopropyl-3-{1-[(6-methyl-2-pyridinyl)methyl]piperidin-4-yl}-3,4-dihydro-2(1H)-quinazolinone Into a solution of 150 mg (0.548 mmol) of 4-isopropyl-3-(piperidin-4-yl)-3,4-dihydro-2(1H)-quinazolinone in 6 ml of dichloromethane, 135 mg (1.10 mmol) of 6-methylpyridin-2-carbaldehyde were added and stirred at room temperature for one hour. Three hundred and fifty milligrams (350 mg, 1.65 mmol) of sodium triacetoxyborohydride were added thereto, and further stirred for 2 hours. After the reaction mixture was diluted with 10 ml of dichloromethane, 20 ml of 5% aqueous sodium hydroxide solution were added. The separated aqueous layer was extracted with dichloromethane, and the combined organic layers were dried over anhydrous sodium sulfate and concentrated under reduced pressure. The concentrated residue was purified by silica gel chromatography to give 170 mg (0.44 mmol) of a racemate of the above-titled compound.

$^1$H-NMR δ (CDCl$_3$): 0.73 (3H, d, J=7.0 Hz), 0.89 (3H, d, J=7.0 Hz), 2.55 (3H, s), 3.64 (2H, s), 4.11 (1H, m), 6.66 (1H, d, J=7.7 Hz), 7.02 (1H, d, J=7.5 Hz), 7.54 (1H, t, J=7.6 Hz)

By separation of high pressure liquid chromatography with optically active column under the following condition, the prior eluent was separated from 170 mg of the above racemate and purified to give 51 mg of the above-titled compound.

Column: about 25 cm of length, about 20 mm of internal diameter, stainless tube packed with aminopropyl silica gel having about 5 μm of particle diameter chemically bonded with N-[(R)-1-(α-naphthyl)ethylaminocarbonyl]-L-tert-leucine having about 5 μm of particle diameter (commercial name SUMICHIRAL OA-4700 (Sumika Chemical Analysis Service))

Mobile phase: hexane/chloroform/methanol=92/6/2
Flow rate: 20 ml/min
Detected wave length: 254 nm Recrystallization of 50 mg of the above-titled compound from 0.5 ml of acetonitrile gave 40 mg of columnar crystals.

mp: 144-145° C. $[α]_D^{25}$+51.3° (c=1, methanol) Hydrochloride:

mp: 160-162° C. (decomposition)

Reference Example 1

Preparation of 1-benzyl-4-{[2-methyl-1-(2-trichloroacetylaminophenyl)]-1-propenylamino}piperidine Into a solution of 11.0 g (35.6 mmol) of isopropyl 2-trichloroacetylaminophenyl ketone, 24.8 ml (178 mmol) of triethylamine and 10.2 g (53.5 mmol) of 4-amino-1-benzylpiperidine in 280 ml of tetrahydrofuran, 7.44 g (39.2 mmol) of titanium tetrachloride were added dropwise under ice-cooling and stirred at room temperature for 24 hours. Aqueous 5% sodium bicarbonate solution and ethyl acetate were added and stirred. The separated oil layer was washed with saturated brine, dried over anhydrous sodium sulfate and concentrated under reduced pressure. The concentrated residue was purified by silica gel chromatography (hexane/ethyl acetate/triethylamine 15/1/1) to give 6.74 g (14.0 mmol) of the above-titled compound.

$^1$H-NMR δ (CDCl$_3$): 1.25-1.51 (2H, m), 1.58 (3H, s), 1.62 (1H, m), 1.77 (3H, s), 3.43 (2H, s), 8.29 (1H, d, J=7.9 Hz)

Reference Example 2

Preparation of 1-benzyl-4-[2-methyl-1-(2-trichloroacetylaminophenyl) propenylamino]piperidine Into a solution of 6.74 g (14.0 mmol) of 1-benzyl-4-{[2-methyl-1-(2-trichloroacetylaminophenyl)]-1-propenylamino}piperidine in 100 ml of tetrahydrofuran, 8.81 g (140 mmol) of sodium cyanoborohydride and 4.01 ml (70.0 mmol) of acetic acid were added and stirred at room temperature for 28 hours. Aqueous 5% sodium bicarbonate solution and ethyl acetate were added and stirred. The separated oil layer was washed with saturated brine, dried over anhydrous sodium sulfate and concentrated under reduced pressure. The concentrated residue was purified by silica gel chromatography (hexane/ethyl acetate/triethylamine 50/50/4) to give 6.62 g (13.7 mmol) of the above-titled compound.

$^1$H-NMR δ (CDCl$_3$):0.68 (3H, d, J=6.6 Hz), 1.03 (3H, d, J=6.6 Hz), 2.31 (1H, br), 3.44-3.54 (3H, m), 8.27 (1H, d, J=8.3 Hz), 13.14 (1H, br)

Reference Example 3

Preparation of 4-isopropyl-3-(1-benzylpiperidin-4-yl)-3,4-dihydro-2(1H)-quinazolinone Into a solution of 6.58 g (13.6 mmol) of 1-benzyl-4-[2-methyl-1-(2-trichloroacetylaminophenyl)propylamino]piperidine in 136 ml of dimethylformamide, 9.42 g (68 mmol) of potassium carbonate were added and stirred at 90° C. for 5 hours. The reaction mixture was cooled to room temperature, and then 0.5% aqueous potassium carbonate solution and ethyl acetate-toluene (1:1) were added thereto and stirred. The separated oil layer was washed with saturated brine, dried over anhydrous sodium sulfate and concentrated under reduced pressure. The concentrated residue was purified by silica gel column chromatography (chloroform/methanol 100/2) to give 3.65 g (10.0 mmol) of the above-titled compound.

$^1$H-NMR δ (CDCl$_3$): 0.73 (3H, d, J=6.8 Hz), 0.89 (3H, d, J=7.0 Hz), 1.80 (1H, m), 3.01 (2H, m), 4.25 (2H, s), 4.32 (1H, d, J=3.6 Hz), 6.97 (1H, d, J=7.0 Hz), 9.14 (1H, s), 9.95 (1H, br)

Reference Example 4

Preparation of 4-isopropyl-3-(piperidin-4-yl)-3,4-dihydro-2(1H)-quinazolinone

Into a solution of 2.30 g (6.33 mmol) of 4-isopropyl-3-(1-benzylpiperidin-4-yl)-3,4-dihydro-2(1H)-quinazolinone in 127 ml of methanol, 0.23 g (0.11 mmol) of 10% palladium carbon (50% wet) and 1.60 g (25.3 mmol) of ammonium formate were added and refluxed under stirring and heating for 4 hours. After cooling to room temperature, the reaction mixture was filtered. To the filtrate, 0.5% aqueous sodium hydroxide solution and chloroform were added and stirred. The separated oil layer was dried over anhydrous sodium sulfate and concentrated under reduced pressure. The concentrated residue was purified by silica gel column chromatography (chloroform/methanol/triethylamine 90/10/5) to give 1.73 g (6.33 mmol) of the above-titled compound.

$^1$H-NMR δ (CDCl$_3$): 0.75 (3H, d, J=6.9 Hz), 0.90 (3H, d, J=6.9 Hz), 1.62-1.66 (1H, m), 4.12 (1H, m), 4.30 (1H, d, J=3.9 Hz), 6.73 (1H, d, J=7.7 Hz), 7.54 (1H, s)

Test Example

Effect on Rhythmic Contractions of Bladder

This test was carried out by some modification of the method of Hedge et al. [Hedge S S. Choppin A. Bonhaus D. Briaud S. Loeb M. Moy T M. Loury D. Eglen R M., British Journal of Pharmacology. 120(8):1409-18, 1997]. Female SD-rats were subjected to abdominal midline incision under urethane anesthesia (0.6 g/kg, s.c. and i.p.), the ureters were ligated, and its kidney side was cut off. A polyethylene cannula was inserted from the urethra into the bladder and the urethra was ligated. The other end of the cannula was connected to a three way connector, to which a constant infusion pump having a 20 ml attached syringe and a pressure transducer for cystometry were also connected. A cannula for administration of a test sample was inserted into the jugular vein and a cannula for measurement of blood pressure and heart rate was inserted into the carotid artery. The intravesical pressure, blood pressure and heart rate were continuously recorded on a polygraph. Physiological saline was infused until rhythmic contractions of the bladder were observed, and after having confirmed stable rhythmic contractions of the bladder, vehicle (10% PEG) and solutions of a test sample dissolved in 10% PEG were administered intravenously in turn from its lower dose. The mean of amplitude and frequency of bladder contraction during a 10-minute period after administration were measured at each dose level, and their rates of change relative to the values obtained when the vehicle alone was administered were calculated, thereby determining $ED_{30}$ values for the contractile amplitude and the contractile frequency, respectively. The results are shown in Table 1. It is apparent from Table 1 that the compounds of the present invention depressed not only the contractile amplitude but also the contractile frequency.

TABLE 1

| Example Nos. | Contractile amplitude: $ED_{30}$ (mg/kg) | Contractile frequency: $ED_{30}$ (mg/kg) |
|---|---|---|
| 1 (Hydrochloride) | 1.71 | 1.31 |
| 2-1 (Hydrochloride) | 1.09 | 0.70 |
| 2-3 (Hydrochloride) | 1.10 | 1.54 |
| 2-4 (Hydrochloride) | 1.42 | 1.35 |
| 3 (Hydrochloride) | 0.94 | 1.79 |

INDUSTRIAL APPLICABILITY

The compounds of the present invention have not only a selective antagonism for the M3 muscarinic receptor but also a depressant action on the frequency of rhythmic bladder contractions, and they are useful for the treatment of pollakiuria and urinary incontinence.

The invention claimed is:

1. An optically active (+) form of the quinazolinone derivatives represented by the general formula (1):

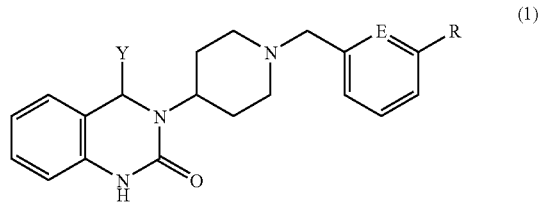

(1)

wherein Y represents a C2-C7 alkyl group; E represents a nitrogen atom; and R represents a fluorine atom, C1-C4 alkyl group, C1-C4 alkoxy group, trifluoromethoxy group or 2,2,2-trifluoroethoxy group, or pharmaceutically acceptable salt thereof.

2. The optically active form of the quinazolinone derivatives described in claim 1, wherein Y is a C3-C7 alkyl group, or pharmaceutically acceptable salt thereof.

3. (+)-3-{1-[3-(2,2,2-trifluoroethoxy)benzyl]piperidin-4-yl}-4-phenyl-3,4dihydro-2(1H)-quinazolinone or pharmaceutically acceptable salt thereof.

4. (+)-3-[1-(3-trifluoromethoxybenzyl)piperidin-4-yl]-4-phenyl-3,4-dihydro-2(1H)-quinazolinone or pharmaceutically acceptable salt thereof.

5. (+)-4-isopropyl-3-{1-[(6-methyl-2-pyridinyl)methyl]piperidin-4-yl}-3,4dihydro-2(1H)-quinazolinone or pharmaceutically acceptable salt thereof.

6. (+)-3-[1-(3-trifluoromethoxybenzyl)piperidin-4-yl]-4-phenyl-3,4dihydro-2(1H)-quinazolinone fumarate.

7. A medicament comprising the compound described in any of claims 1 or 3-6 or pharmaceutically acceptable salt thereof.

8. A method for treating pollakiuria or urinary incontinence which comprises administrating an effective amount of the compound described in any of claims 1 or 3-6 or pharmaceutically acceptable salt thereof to a patient in need.

9. A medicament comprising the optically active form of the quinazolinone derivatives described in claim 1, wherein Y is C3-C7 alkyl group, or pharmaceutically acceptable salt thereof.

10. A medicament comprising the optically active form of the quinazolinone derivatives described in claim 1, wherein Y is C3-C7 alkyl group, or pharmaceutically acceptable salt thereof.

11. A method for treating pollakiuria or urinary incontinence which comprises administrating an effective amount of the optically active derivatives described in claim 1, wherein Y is C3-C7 alkyl group, or pharmaceutically acceptable salt thereof to a patient in need.

12. A method for treating pollakiuria or urinary incontinence which comprises administrating an effective amount of the optically active derivatives described in claim 1, wherein Y is C3-07 alkyl group, or pharmaceutically acceptable salt thereof to a patient in need.

* * * * *